United States Patent [19]

Cohnen

[11] Patent Number: 4,864,061
[45] Date of Patent: Sep. 5, 1989

[54] SUBSTITUTED PHENOXYALKANOLAMINES AND PHENOXYALKANOL-CYCLOALKYLAMINES, AND INTERMEDIATE PRODUCTS

[75] Inventor: Erich Cohnen, Hamburg, Fed. Rep. of Germany

[73] Assignee: Beiersdorf Aktiengesellschaft, Hamburg, Fed. Rep. of Germany

[21] Appl. No.: 883,208

[22] Filed: Jul. 8, 1986

Related U.S. Application Data

[63] Continuation of Ser. No. 722,906, Apr. 12, 1985, abandoned, which is a continuation of Ser. No. 450,161, Dec. 16, 1982, abandoned.

[30] Foreign Application Priority Data

Dec. 23, 1981 [DE] Fed. Rep. of Germany ....... 3151201

[51] Int. Cl.[4] ............................................. C07C91/10
[52] U.S. Cl. .................................................. 564/349
[58] Field of Search ............... 564/349, 347, 584, 351; 568/442, 586, 587; 250/501.17; 514/652; 260/501.17

[56] References Cited

U.S. PATENT DOCUMENTS

| | | | |
|---|---|---|---|
| 3,501,769 | 3/1970 | Crowther et al. | 564/349 X |
| 3,640,067 | 2/1972 | Narayanan et al. | 564/349 X |
| 3,873,600 | 3/1975 | Brandstrom et al. | 564/349 X |
| 4,145,442 | 3/1979 | Berntsson et al. | 564/349 X |
| 4,171,370 | 10/1979 | Jonas et al. | 564/349 X |
| 4,243,681 | 1/1981 | Morrow et al. | 564/349 X |
| 4,342,783 | 8/1982 | Morselli et al. | 514/652 |
| 4,402,976 | 9/1983 | Muir | 514/652 X |
| 4,515,814 | 5/1985 | Wick et al. | 514/652 |
| 4,522,829 | 6/1985 | Harting et al. | 514/652 |

FOREIGN PATENT DOCUMENTS

| | | |
|---|---|---|
| 082461 | 3/1987 | European Pat. Off. . |
| 2649605 | 5/1977 | Fed. Rep. of Germany . |
| 2081523 | 12/1971 | France . |
| 2139740 | 1/1973 | France . |
| 2289172 | 5/1976 | France . |

OTHER PUBLICATIONS

Goodman et al., The Pharmacological Basis of Therapeutics, 6th Ed., (1980) pp. 113, 114, 188, 189.
The Merck Index, 9th Ed. (1976) p. ONR-42.
The Mercl Index, 10th Ed. (1983) pp. 1203 & 6031.
Schid, Brit. J. Pharmacol., vol. 2 (1947) pp. 189–206.
Lumley et al., J. Pharmac., vol. 29 (1977), pp. 598–604.

Primary Examiner—Richard L. Raymond
Attorney, Agent, or Firm—Sprung Horn Kramer & Woods

[57] ABSTRACT

New substituted phenoxyalkanolamines and phenoxyalkanol-cycloalkylamines of the general formula I

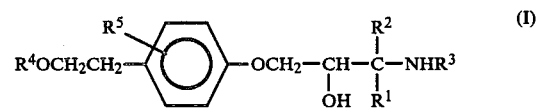

in which $R^1$ and $R^2$, which can be identical or different, denote alkyl groups with in each case 1 to 4 carbon atoms, or $R^1$ and $R^2$ together denote the group —$(CH_2)_n$—, wherein n is the number 4 or 5, $R^3$ denotes hydrogen, or an alkyl group or an acyl group with in each case 1 to 6 carbon atoms, $R_4$ denotes an alkyl group with 1 to 4 carbon atoms or the cyclopropylmethyl group and $R^5$ denotes hydrogen halogen or alkyl, and acid addition salts thereof, have a cardioselective $\beta_1$-adrenolytic and hypotensive action. They can be used as medicaments for the treatment of angina pectoris, hypertension and arrhythmias.

8 Claims, No Drawings

SUBSTITUTED PHENOXYALKANOLAMINES AND PHENOXYALKANOL-CYCLOALKYLAMINES, AND INTERMEDIATE PRODUCTS

This is a continuation of application Ser. No. 722,906 filed 4/12/85, now abandoned, which is a continuation of Ser. No. 450,161 filed 12/16/82, now abandoned.

The invention relates to new substituted phenoxyalkanolamines and phenoxyalkanol-cycloalkylamines of the general formula I

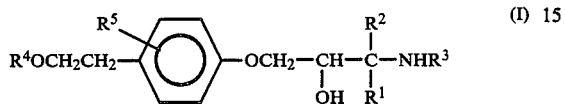

in which $R^1$ and $R^2$, which can be identical or different, denote alkyl groups with in each case 1 to 4 carbon atoms, or $R^1$ and $R^2$ together denote the group —(CH$_2$)$_n$—, wherein n is the number 4 or 5, $R^3$ denotes hydrogen, or an alkyl group or an acyl group with in each case 1 to 6 carbon atoms, $R^4$ denotes an alkyl group with 1 to 4 carbon atoms or the cyclopropylmethyl group and $R^5$ denotes hydrogen, halogen or alkyl, and acid addition salts thereof, processes for their preparation and their use in pharmacetical products.

The invention furthermore relates to new substituted phenoxynitroalkanols and phenoxyhydroxyalkylnitrocycloalkanes of the general formula II

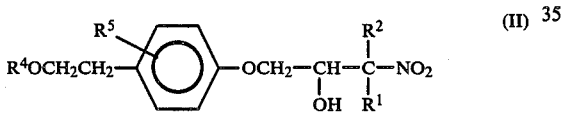

in which $R^1$ and $R^2$, which can be identical or different, denote alkyl groups with in each case 1 to 4 carbon atoms, or $R^1$ and $R^2$ together denote the group —(CH$_2$)$_n$—, wherein n is the number 4 or 5, $R^4$ denotes an alkyl group with 1 to 4 carbon atoms or the cyclopropylmethyl group and R$_5$ denotes hydrogen, halogen or alkyl, processes for their preparation and their use as intermediate products for the preparation of the compounds of the general formula I according to the invention.

The intermediate products of the formula II also have therapeutic properties. In particular, they can be used like the end products of the general formula I according to the invention.

The new compounds of the general formulae I and II contain one or two asymmetric carbon atoms. The invention thus also relates to various optical isomers and the diastereo isomers, as well as the addition salts of these compounds with acids. Racemates can be resolved into their optical antipodes by methods which are known per se, for example by using optically active acids, such as tartaric acid, camphorsulphonic acid or dibenzoyltartaric acid, or as esters or ethers with optically active components or via compounds which include urea.

The invention furthermore relates to new substituted phenoxyacetaldehydes of the general formula III

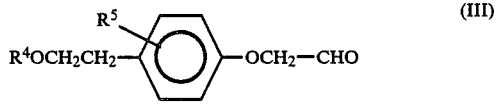

in which $R^4$ denotes an alkyl group with 1 to 4 carbon atoms or the cyclopropylmethyl group and $R^5$ denotes hydrogen, halogen or alkyl, processes for their preparation and their use as intermediate products for the preparation of the compounds of the general formulae I and II according to the invention.

Compounds which block beta-receptors but do not have the substituents, according to the invention, of the α-carbon atom in the propoxy side chain are already known from German Offenlegungsschriften Nos. 2,106,209 and 2,649,605.

The definition chosen here for the alkyl radicals $R^1$, $R^2$, $R^3$, $R^4$ and $R^5$ and the alkyl radicals of the acyl group $R^3$ means both straight-chain and branched aliphatic hydrocarbon radicals containing 1 to 6 carbon atoms, such as, for example, the methyl group, ethyl group, n-propyl group, isopropyl group, n-butyl group, sec.-butyl group, isobutyl group, tert.-butyl group, n-pentyl group, isopentyl group, neopentyl group, amyl group, n-hexyl group and isohexyl groups and the branched hexyl groups with a quaternary carbon atom. The methyl group, the ethyl group and the propyl groups are particularly preferred.

$R^4$ is preferably methyl, ethyl, isopropyl or cyclopropylmethyl.

Preferred acyl groups are alkanoyl groups with 1 to 6 carbon atoms, in particular the formyl group, the acetyl group and the propionyl groups.

The radical $R^5$ is preferably in the 2-position of the phenyl group or in the ortho-position relative to the 2-hydroxy-3-amino-alkoxy side chain. The halogen radical $R^5$ is fluorine, chlorine, bromine or iodine, but in particular chlorine or bromine. The preferred alkyl radical $R^5$ are methyl and ethyl. $R^5$ can also preferably be hydrogen.

Preferred compounds of the formulae I and II according to the invention are those which, with the definition that $R^1$ and $R^2$ together denote the alkylidene groups —(CH$_2$)$_n$—, wherein n is 4 or 5, contain a cyclopentane ring or cyclohexane ring. With this definition, they are each formed including the α-carbon atom of the propoxy side chain.

Moreover, compounds of the formulae I and II in which $R^1$ and $R^2$ denote alkyl, in particular methyl, and also compounds in which $R^1$ and $R^2$ are alkyl groups, in particular methyl groups, and $R^4$ is methyl or cyclopropylmethyl are preferred.

The new compounds of the general formula I according to the invention and their acid addition salts have valuable therapeutic properties. They are distinguished by a cardioselective $R_1$-adrenolytic action and hypotensive properties and are particularly suitable for the treatment of angina pectoris, hypertension and cardiac arrhythmias. They are furthermore suitable for the treatment of glaucoma, since they reduce the intraocular pressure.

The surprisingly high cardioselectivity of the new compounds depends, inter alia, on the di-substitution of the α-carbon atom of the propoxy chain. Compounds in which $R^3$ denotes a hydrogen atom have been found to be particularly valuable in this connection. $R^1$ and $R^2$ are then preferably alkyl groups, in particular methyl groups.

The following compounds of the general formula I and salts thereof with a high therapeutic effect are particularly preferred, and in particular in the form of the racemates and in the form of optically active isomers: 1-[4-(2-methoxyethyl)-phenoxy]-3-amino-3-methyl-butan-2-ol and 1-[4-(2-cyclopropylmethoxyethyl)-phenoxyl]-3-amino-3-methyl-butan-2-ol.

The compounds of the present invention can be used orally or parenterally in humans in a dosage of 20 mg to 1 g, preferably 50 mg to 500 mg, per day in particular in divided doses, for example two or three times daily. In cats an intravenous dose of 1 to 10 mg/kg lowers tachycardia caused by isoprenaline by 25% ($ED_{25}$). For 1-[4-(2-methoxyethyl)-phenoxy]-3-amino-3-methyl-butan-2-ol, this dose is 1.75 mg.

The daily dose is to be matched to the individual, because it depends on the receptor sensitivity and the sympathicotonia of the patient. Advantageously, the treatment is started with low doses and then increased.

For the treatment of hypertension, daily doses of 50 to 200 mg, divided into two or three administrations, are preferred. Angina pectoris is preferably treated with 50 to 200 mg per day, divided into two adminstrations. For combating disorders in cardiac rhythm, 200 to 400 mg are administered daily, divided into two or three administrations.

For the treatment of increased intra-ocular pressure, 0.1 to 4% strength aqueous isotonic solutions are applied locally to the eye in dosages of one or more drops once or several times daily.

Pharmaceutical formulations which contain a compound of the formula I or pharmaceutically acceptable salts thereof, together with a pharmaceutically acceptable diluent or excipient, are provided according to the invention.

The compounds according to the invention can be mixed with the customary pharmaceutically acceptable diluents or excipients and, if appropriate, with other auxiliaries, and can be administered, for example, orally or parenterally. They can be administered orally in the form of tablets, dragees, syrups, suspensions and liquids, or parenterally in the form of solutions or suspensions. Products to be administered orally can contain one or more additives, such as sweeteners, aromatising agents, colorants and preservatives. Tablets can contain the active compound mixed with the customary, pharmaceutically acceptable auxiliaries, for example inert diluents, such as calcium carbonate, sodium carbonate, lactose and talc, granulating agents and agents which promote disintegration of the tablets on oral administration, such as starch or alginic acid, binders, such as starch or gelatin, and lubricants, such as magnesium stearate, stearic acid and talc.

Examples of suitable excipients are milk sugar (lactose), gelatin, maize starch, stearic acid, ethanol, propylene glycol, ethers of tetrahydrofuryl alcohol and water.

The tablets can be coated by known procedures, in order to delay disintegration and resorption in the gastrointestinal tract, which means the activity of the active compound can extend over a longer period of time. The active compound in the suspensions can also be mixed with auxiliaries which are customary for the preparation of such compositions, for example suspending agents, such as methylcellulose, tragacanth or sodium alginate, wetting agents, such as lecithin, polyethylene stearate and polyoxyethylene sorbitan monooleate, and preservatives, such as ethyl para-hydroxybenzoate. Capsules can contain the active compound as the only constituent or as a mixture with a solid diluent, such as calcium carbonate, calcium phosphate or kaolin. The injectable products are likewise formulated in a manner which is known per se. The pharmaceutical products can contain the active compound in an amount of 0.1 to 90%, in particular 1 to 90%, the remainder being an excipient or additive. In view of the preparation and administration, solid products, such as tablets and capsules, are preferred. The products preferably contain the active compound in an amount of 50–100 mg.

The compounds of the general formula I can be obtained by the following processes:

The process for the preparation of the phenoxyalkanolamines and phenoxyalkanol-cycloalkylamines according to the general formula I, with the abovementioned meaning of the radical $R^1$ to $R^5$, is characterised in that compounds of the general formula II

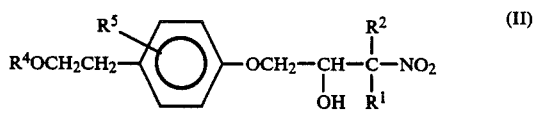

with the abovementioned meaning of $R^1$, $R^2$, $R^4$ and $R^5$, are reduced and, if appropriate, the amino group formed is alkylated or acylated.

The reduction is carried out either with palladium/hydrogen is alcoholic solution in the presence of glacial acetic acid at 20° to 100° C. and under 5 to 10 bar, or with zinc/hydrochloric acid at temperatures between 50° to 70° C.

The amino group is alkylated either with an alkylating agent, such as, for example, dialkyl sulphate or tosyl alkyl esters, or by reaction with an aldehyde and subsequent reduction of the azomethine with a borohydride.

The methyl group ($R^3 = CH_3$) is most advantageously introduced by formylation of the amino group with formic acid/acetic anhydride and subsequent reduction of the formamide with lithium aluminium hydride.

The acyl groups are introduced with corresponding carboxylic acid anhydrides or carboxylic acid chlorides in the presence of a basic catalyst, or by heating the components. The acyl esters which may be formed are split by alkaline hydrolysis.

The process for the preparation of the phenoxynitroalkanols and phenoxyhydroxyalkyl-nitrocycloalkanes according to the general formula II, with the abovementioned meaning of the radicals $R^1$, $R^2$, $R^4$ and $R^5$, is characterised in that compounds of the general formula III

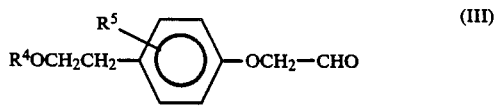

with the abovementioned meaning of $R^4$ and $R^5$, are reacted with compounds of the general formula IV $$\begin{array}{c} R^1 \\ | \\ CH-NO_2 \\ | \\ R^2 \end{array} \quad (IV)$$

with the abovementioned meaning of $R^1$ and $R^2$.

The nitroalkanes, or nitrocyclopentane and nitrocyclohexane of the formula IV are condensed with the aldehyde of the formula III in alcoholic solution in the presence of sodium alcoholate at room temperature.

The nitro compounds of the formula IV are known, or they can be obtained by known processes.

The process for the preparation of the aldehydes of the general formula III, with the abovementioned meaning of $R^4$ and $R^5$, is characterised in that compounds of the general formula V

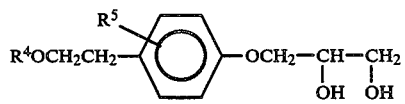

with the meaning given for $R^4$ and $R^5$, are split by oxidation.

The compounds of the formula III are accessible, in particular, from compounds of the general formula V by oxidative splitting with lead-IV acetate in ethyl acetate, benzene or toluene or with sodium meta-periodate in alcohol/water mixtures. The compounds of the formula V used as starting materials are new compounds. They can be prepared from the corresponding known phenols by reaction with 2,3-epoxypropanol with catalytic amounts of a quaternary amine in a solvent or by direct fusion of the reactants at temperatures between 120° to 160° C. They are valuable intermediate products in the preparation of the end products according to the invention. The invention also relates to these new starting materials, the processes for their preparation and their use.

The compounds of the general formula I can be isolated from the reaction mixtures either as bases or in the form of their salts.

As bases, they can be converted into salts with suitable inorganic or organic acids by known processes. Physiologically acceptable salts are preferred. Examples of suitable inorganic acids are hydrogen halide acids, for example hydrochloric acid, or sulphuric acid, and examples of suitable organic acids are fumaric acid and maleic acid. For the preparation, an alcoholic solution of a suitable acid is added to a hot alkaline solution of the base and, after ether has been added, the salt is obtained.

The examples which follow serve to illustrate the invention:

EXAMPLE 1

1-[4-(2-Methoxyethyl)-phenoxy]-3-amino-3-methyl-butan-2-ol 19 g of 1-[4-(2-methoxyethyl)-phenoxy]-3-nitro-3-methyl-butan-2-ol are hydrogenated at 60° C. and under a pressure of 6 bar in a mixture of 250 ml of ethanol and 50 ml of glacial acetic acid in the presence of 4 g of palladium-on-charcoal (10% Pd). After the mixture has been filtered and the solvent has been evaporated off, the residue is rendered alkaline with 2N NaOH and the mixture is extracted with $CH_2Cl_2$. The organic phase is washed with water and dried with $Na_2SO_4$ to give, after evaporation, 15 g of the amine, which is converted into the hydrochloride with ethanol hydrochloric acid. Melting point: 120°–122° C. (ethyl acetate).

The compounds of the general formula I listed in Table 1 are prepared analogously to Example 1 (in these Examples 2 to 5a, $R^5$ is hydrogen):

TABLE 1
($R^5 = H$)

| Example No. | $R^1$ | $R^2$ | $R^3$ | $R^4$ | m.p. °C. | salt |
|---|---|---|---|---|---|---|
| 2 | CH₃ | CH₃ | H | —CH₂—  | 176–177 | fumarate |
| 3 | CH₃ | CH₃ | H | —CH₂CH₂CH₃ | 174–176 | fumarate |
| 3a | CH₃ | CH₃ | H | isopropyl | | fumarate |
| 4 | CH₃ | CH₂CH₃ | H | CH₃ | 156–158 | fumarate |
| 5 | —(CH₂)₄— | | H | CH₃ | 182–183 | fumarate |
| 5a | —(CH₂)₅— | | H | CH₃ | 77–78 | base |

EXAMPLE 6

1-[4-(2-Methoxyethyl)-phenoxy]-3-amino-3-methyl-butan-2-ol 18.3 g of zinc dust are gradually added to 20 g of 1-[4-(2-methoxyethyl)-phenoxy]-3-nitro-3-methyl-butan-2-ol in 400 ml of ethanol and 60 ml of concentrated hydrochloric acid at 50°–60° C. The mixture is stirred at this temperature for one hour and filtered and the solvent is evaporated off. After 200 ml of 40% strength NaOH have been added, the amine is extracted with methylene chloride. The hydrochloride is obtained as described in Example 1.

Melting point: 119°–120° C.

EXAMPLE 6a

1-[2-Chloro-4-(2-methoxyethyl)-phenoxy]-3-amino-3-methyl-butan-2-ol is obtained analogously to Example 6.

Melting point: 184°–186° C. (Fumarate)

EXAMPLE 6b

1-[2-Methyl-4-(2-methoxyethyl)-phenoxy]-3-amino-3-methyl-butan-2-ol is obtained analogously to Example 6.

EXAMPLE 7

1-[4-(2-Methoxyethyl)-phenoxy]-3-methylamino-3-methyl-butan-2-ol 15 ml of acetic anhydride are added dropwise to 5.1 g of 1-[4-(2-methoxyethyl)-phenoxy]-3-amino-3-methyl-butan-2-ol in 50 ml of formic acid at room temperature. After 15 hours, 10 ml of water are added and the mixture is evaporated to dryness. Customary working up gives 4.5 g of the N-formyl compound in the form of an oil, which is reduced with 2 g of LiAlH₄ in 50 ml of tetrahydrofuran. 3.3 g of the base are obtained, and are converted into the hydrochloride with ethanolic HCl. Melting point: 86°–88° C.

EXAMPLE 8

1-[4-(2-Methoxyethyl)-phenoxy]-3-hexylamino-3-methyl-butan-2-ol 5.1 g of 1-[4-(2-methoxyethyl)-phenoxy]-3-amino-3-methyl-butan-2-ol are recated with 2.2 g of caproaldehyde in 50 ml of toluene to give the azomethine, the water being distilled off. After the toluene has been removed, the residue is taken up in 50 ml of methanol and is reduced with 1.9 g of NaBH$_4$ at 10°–15° C.

Customary working up and purification by column chromatography on silica gel gives 5 g of the base, which give 3.9 of the hydrochloride with ethanolic HCl and after crystallisation with ethyl acetate/ether.

Melting point: 135°–137° C.

EXAMPLE 9

1-[4-(2-Methoxyethyl)-phenoxy]-3-isopropylamino-3-methyl-butan-2-ol 5.06 g (0.02 mol) of 1-[4-(2-methoxyethyl)-phenoxy]-3-amino-3-methyl-butan-2-ol are heated to 140° C. with 4.3 g (0.02 mol) of isopropyl toluene-4-sulfphonate for two hours. After 100 ml of toluene and 100 ml of 2N NaOH have been added, the mixture is stirred for one hour and the toluene phase is separated off, shaken with water and evaporated in vacuo. Column chromatography on silica gel gives 3.5 g of the abovementioned compound, which is converted into the hydrochlorie with ethanolic HCl.

EXAMPLE 10

1-[4-(2-Methoxyethyl)-phenoxy]-3-acetamido-3-methyl-butan-2-ol 5.7 g of 1-[4-(2-Methoxyethyl)-phenoxy]-3-amino-3-methyl-butan-2-ol are stirred with 30 ml of acetic anhydride at room temperature for 2 hours and, after the excess anhydride has been removed, the residue is left to stand in 50 ml of 1N methanolic sodium hydroxide solution for 15 hours. Customary working up gives 5.1 g of the acetamido compound.

EXAMPLE 10

1-[4-(2-Methoxyethyl)-phenoxy]-3-nitro-3-methyl-butan-2-ol 39.5 g of 2-nitropropane and 27 g of 4-(2-methoxyethyl)-phenoxy-acetaldehyde are successively added dropwise to a solution of 2 g of sodium in 150 ml of methanol. After the mixture has been stirred at room temperature for 15 hours, the solution is poured onto water and acidified with 2N HCl. Extraction with CHCl$_3$ gives, after crystallisation from diisopropyl ether, 23.3 g of the nitro compound mentioned in the title. Melting point: 92°–94° C.

The compounds of the general formula II listed in Table 2 are prepared analogously to Example 11 (in these Examples 12 to 15, R$^5$ is hydrogen:

TABLE 2

| Example No. | R$^1$ | R$^2$ | R$^4$ | m.p. °C. |
|---|---|---|---|---|
| 12 | CH$_3$ | CH$_3$ | —CH$_2$—◁ | 64–66 |
| 13 | CH$_3$ | CH$_3$ | —CH$_2$CH$_2$CH$_3$ | 82–84 |
| 14 | CH$_3$ | CH$_2$CH$_3$ | CH$_3$ | oil |
| 15 | —(CH$_2$)$_4$— | | CH$_3$ | oil |

EXAMPLE 16

4-(2-Methoxy-ethyl)-phenoxy-acetaldehyde 39 g of 4-(2-methoxy-ethyl)-phenol are heated to about 120° C., after addition of 0.5 g of benzyltributylammonium chloride, and 20.4 g of 2,3-epoxypropanyl are added dropwise in the course of 15 minutes. The mixture is allowed to cool, the syrup is dissolved in CHCl$_3$, the solution is washed with water and the CHCl$_3$ residue is purified by preparative HPLC. 50 g of 3-[4-(2-methoxyethyl-phenoxy]-propane-1,2-diol are obtained.

Melting point: about 25° C.

A solution of 2.5 g of sodium meta-periodate in 100 ml of water and 13 ml of 0.1N boric acid is added dropwise to 12 g of the above diol in 100 ml of ethanol at 10°–15° C. After one hour, the NaIO$_3$ is filtered off, the filtrate is diluted with water and the aldehyde is extracted with CHCl$_3$. After the solvent has been evaporated off, 11 g of 4-(2-methoxy-ethyl)-phenoxyacetaldehyde remain as the mono-ethyl acetal.

Melting point of the 2,4-dinitrophenylhydrazone: 106°–108° C.

EXAMPLE 17

Preparation of tablets

Tablets which contain the constituents given below are prepared by known procedures. These are suitable for the treatment of hypertension in a dosage of 50 mg twice daily, for the treatment of angina pectoris in an amount of 50 mg twice daily, and for the treatment of arrhythmias in an amount of 100 mg three times daily.

| | Tablet A | Tablet B |
|---|---|---|
| 1-[4-(2-Methoxyethyl)-phenoxy]-3-amino-3-methyl-butan-2-ol | 50 mg | 100 mg |
| Lactose | 189 mg | 134 mg |
| Maize starch | 25 mg | 25 mg |
| Magnesium stearate | 1 mg | 1 mg |

EXAMPLE 18

Preparation of eye drops

Eye drops which contain the following constituents can be prepared in a known manner. They can be used in a dose of one to two drops per eye once or twice daily, preferably one drop twice daily:

1-[4-(2-Methoxyethyl)-phenoxy]-3-amino-3-methylbutan-2-ol 0.5 g

Isotonic aqueous solution (Ringer's solution) to 100 ml.

I claim:

1. Substituted phenoxyalkanolamines and phenoxyalkanol-cycloalkylamines of the general formula I

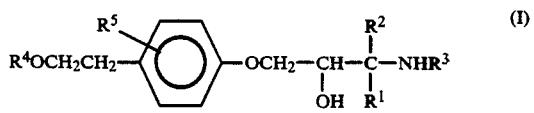

in which R$^1$ and R$^2$, which can be identical or different, denote alkyl groups with in each case 1 to 4 carbon atoms, or R$^1$ and R$^2$ together denote the group —(CH$_2$)$_n$—, wherein n is the number 4 or 5, R$^3$ denotes hydrogen, R$^4$ denotes an alkyl group with 1 to 4 carbon atoms or the cyclopropylmethyl group and R$^5$ denotes hydrogen, halogen or alkyl, and acid addition salts thereof.

2. Phenoxyalkanolamines and phenoxyalkanol-cycloalkylamines according to claim 1, of the general formula I, in which R$_1$ and R$_2$ each denote alkyl.

3. Phenoxyalkanolamines and phenoxyalkanol-cycloalkylamines according to claim 1 of the general formula I, in which R$^1$ and R$^2$ each denote methyl and R$^4$ is methyl or cyclopropylmethyl.

4. Phenoxyalkanolamines and phenoxyalkanol-cycloalkylamines according to claim 1 of the general formula I, in which $R^5$ denote hydrogen.

5. A compound of claim 1 which is 1-[4-(2-methoxyethyl)-phenoxy]-3-amino-3-methyl-butan-2-ol.

6. A compound of claim 1 which is 1-[4-(2-cyclopropylmethoxyethyl)-phenoxy]-3-amino-3-methyl-butan-2-ol.

7. Substituted phenoxynitroalkanols and phenoxyhydroxyalkyl-nitrocycloalkanes of claim 1 of the general formula II

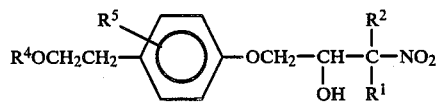
(II)

in which $R^1$ and $R^2$, which can be identical or different, denote alkyl groups with in each case 1 to 4 carbon atoms, or $R^1$ and $R^2$ together denote the group —(CH$_2$)$_n$—, wherein n is the number 4 to 5, $R^4$ denotes an alkyl group with 1 to 4 carbon atoms or the cyclopropylmethyl group and $R^5$ denotes hydrogen, halogen or alkyl.

8. Substituted phenoxyacetaldehydes of claim 1 of the general formula III

(III)

in which $R^4$ denotes an alkyl group with 1 to 4 carbon atoms or the cyclopropylmethyl group and $R^5$ denotes hydrogen, halogen or alkyl.

* * * * *